(12) United States Patent
Matsuzawa et al.

(10) Patent No.: US 8,596,782 B2
(45) Date of Patent: Dec. 3, 2013

(54) BASKET FOR HOLDING A MEDICAL DEVICE

(75) Inventors: Yasuo Matsuzawa, Roswell, GA (US); Lynn Cook Winterton, Alpharetta, GA (US); Michael Nelson Wilde, Kennesaw, GA (US)

(73) Assignee: Novartis AG, Basel (CH)

( * ) Notice: Subject to any disclaimer, the term of this patent is extended or adjusted under 35 U.S.C. 154(b) by 4330 days.

(21) Appl. No.: 10/152,930

(22) Filed: May 22, 2002

(65) Prior Publication Data

US 2003/0024829 A1 Feb. 6, 2003

Related U.S. Application Data

(60) Provisional application No. 60/292,997, filed on May 23, 2001, provisional application No. 60/305,684, filed on Jul. 16, 2001.

(51) Int. Cl.
  *G02C 7/04* (2006.01)
  *A45C 11/04* (2006.01)

(52) U.S. Cl.
  USPC ........................................ 351/159.33; 206/5.1

(58) Field of Classification Search
  USPC ........................ 206/5.1; 351/159.02, 159.33
  See application file for complete search history.

(56) References Cited

U.S. PATENT DOCUMENTS

| | | | |
|---|---|---|---|
| 4,700,729 A * | 10/1987 | Thaler | 134/139 |
| 5,080,839 A | 1/1992 | Kindt-Larsen | 264/2.6 |
| 5,094,609 A | 3/1992 | Kindt-Larsen | 425/445 |
| 5,101,967 A | 4/1992 | Sibley | 206/5.1 |
| 5,874,127 A | 2/1999 | Winterton et al. | 427/164 |
| 6,000,534 A * | 12/1999 | Koomruian, Jr. | 206/5.1 |
| 6,347,870 B1 | 2/2002 | LaRuffa | 351/177 |
| 6,695,988 B1 * | 2/2004 | Schlagel et al. | 264/2.6 |

FOREIGN PATENT DOCUMENTS

| EP | 0 476 937 B1 | 8/1995 |
|---|---|---|
| WO | WO 01/32408 A2 | 5/2001 |

OTHER PUBLICATIONS

International Search Report; PCT/EP02/05620; Oct. 10, 2002.

* cited by examiner

*Primary Examiner* — Scott J Sugarman
(74) *Attorney, Agent, or Firm* — Robert Ambrose

(57) ABSTRACT

An embodiment of the invention is a basket for holding ophthalmic lenses. A basket of the present invention has a lattice structure having a lens contacting side and an opposite lens non-contacting side, wherein the lens-contacting side of the lattice has a very sharp edge structure and the lens non-contacting side can be a normal solid surface to maintain the mechanical strength of the basket. A tray that comprises a plurality of baskets is another embodiment of the invention. In addition, the invention provides a stack assembly that comprises a plurality of trays each of which comprises a plurality of baskets.

8 Claims, 9 Drawing Sheets

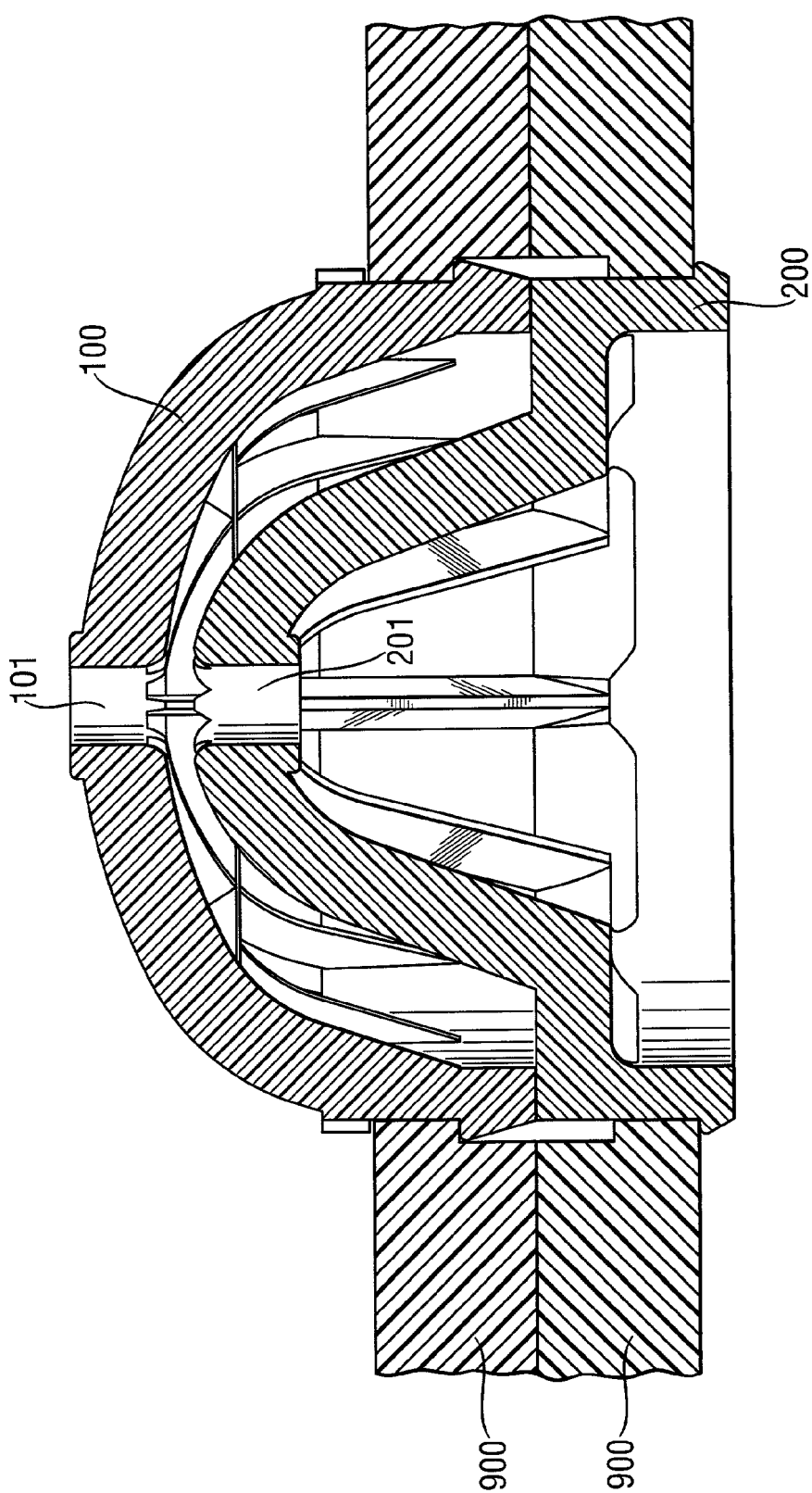

BASKET FOR HOLDING A MEDICAL DEVICE

This application claims the benefits under 35 USC §119(e) of United States provisional application Ser. Nos. 60/292,997 filed May 23, 2001, and 60/305,684 filed Jul. 16, 2001, incorporated herein by reference in their entireties.

The present invention provides a basket and tray for holding a medical device, especially ophthalmic lenses. The basket or tray of the present invention is useful in the manufacture of medical devices, especially ophthalmic lenses, involving operations including but not limited to washing, extracting, coating and the like.

BACKGROUND

Many devices used in biomedical applications require that the bulk of the device have one property, while the surface of the device has another property. For example, contact lenses may have high oxygen permeability through the lens to maintain good corneal health. However, materials that exhibit exceptionally high oxygen permeability (e.g. polysiloxanes) are typically hydrophobic and will adhere to the eye. Thus, a contact lens generally has a core or bulk material that is highly oxygen permeable and hydrophobic, and a surface that has been treated or coated to increase hydrophilic properties, thereby allowing the lens to freely move on the eye without binding excessive amounts of tear lipid and protein.

In order to modify the hydrophilic nature of a relatively hydrophobic contact lens material, a coating may be applied onto the surface of a contact lens using a number of technologies, including a plasma treatment process, a Langmuir-Blodgett deposition process, a controlled spin casting process, a chemisorption process, a vapor deposition or a layer-by-layer polymer adsorption process.

The layer-by-layer polymer adsorption (LbL) process could be one useful process for increasing hydrophilic properties of contact lenses. By dipping iteratively one or more lenses in an alternating fashion to a polyanion (e.g., polyacrylic acid, PAA) solution and then a polycation (polyallylamine hydrochloride, PAH) solution, a LbL coating can be formed on the surfaces of lenses. A LbL coating on an ophthalmic lens can increase hydrophilic properties and thereby allow the lens to freely move on the eye without binding excessive amounts of tear lipid and protein. The on-eye movement is one of important criteria for wearing comfort.

Generally, LbL coating of lenses is carried out with the help of lens-carrying cages which each comprise a male and female basket halves. Many such cages can be affixed together to form trays of baskets. Such trays may then be placed side-by-side to allow hundreds or thousands of lenses to be simultaneously processed with a coating solution. Such trays may also be used in other manufacturing processes of ophthalmic lenses, such as washing, extracting, coating, drying and the like.

Currently, various types of fixtures and baskets are used for holding lenses in those manufacturing processes. Generally, such baskets are made of a plastic but it can be made of any fabricated material. The structure of a basket can be a pair of half-spheres, which have curved surfaces to fit the curvature of an ophthalmic lens. The curved surface is not a solid blank piece. It is partially cut open so that a fluid such as washing solution, water, or extraction media, can freely pass through the basket while an ophthalmic lens is held in place. Currently available baskets with a lattice network structure generally have a percentage of opening surface over total surface being in the range of 25%-50%. This would give a sufficient fluid flow while holding ophthalmic lens in place during a process.

However, those currently available baskets still have a relatively high percentage of solid surface available for a lens to contact. It is known that ophthalmic lenses may tend to stick to the solid surface of baskets under contact because of hydrophobic-hydrophobic interactions and/or bindings between surface oligomers. A high percentage of solid surface will be susceptible to the adhesion of a lens to a basket and prevent the lens from being treated uniformly during a washing, extracting, coating, or drying process. This could affect the efficiency of a process for treating lenses and therefore could be a problem for the production. Therefore, there is a need for a basket with a design that could minimize and/or eliminate the adhesion of a lens onto a basket.

Furthermore, when a lens-holding basket or tray is used in a LbL coating process, some chemicals such as polyelectrolytes tend to adhere onto the surface of the basket or tray to form an unwanted coating. Such coating on the basket or becomes thicker and brittle as the basket is repeatedly used in LbL coating process. It is very likely that this unwanted coating will flake or fracture off from the basket surface during a LbL coating process. If flakes of the unwanted coating adhere onto a lens to be coated, they can mask some portions of a lens and preventing those portions of lenses from being coated, producing lenses with coating defects. To eliminate this undesirable phenomenon occurring, the unwanted LbL coating needs to be abraded using a physical means. Such physical removal process of the unwanted LbL coatings from baskets is long, tedious and labor intensive and may damage the surfaces of the baskets. Therefore, there is a need for a method of efficiently removing any unwanted coatings on baskets.

An object of the invention is to eliminate such problems by providing an essential "contactless" surface of baskets to ophthalmic lenses.

Another object of the invention is to provide a method for cleaning efficiently baskets or trays containing baskets to remove any unwanted coatings from the surfaces of the baskets or trays without damaging their surfaces.

SUMMARY OF THE INVENTION

An embodiment of the present invention is a basket for holding a medical device. A basket of the present invention has a lattice structure having a medical device-contacting side and an opposite medical non-contacting side, wherein the medical device-contacting side of the lattice has sharp edges available for the medical device to contact. In a preferred embodiment, the sharp edges are thin lines. More preferably, each of the lines has a thickness of about 1/10 mm or less.

Another embodiment of the present invention is a tray comprising a plurality of baskets, wherein each of the basket is capable of holding a medical device and has a lattice structure having a medical device-contacting side and an opposite medical device non-contacting side, wherein the medical device-contacting side of the lattice has sharp edges available for the medical device to contact. In a preferred embodiment, the sharp edges are thin lines. More preferably, each of the thin lines has a thickness of about 1/10 mm or less.

Still another embodiment of the present invention is a method for cleaning a basket for holding a medical device, the method comprising immersing the basket in an aqueous solution containing at least 1% weight/volume of KOH or $N_aOH$ for at least 5 minutes, removing the basket from the aqueous KOH or N$_a$OH solution, and rising the basket with water to remove KOH or N$_a$OH from the surface of the basket.

BRIEF DESCRIPTION OF THE FIGURES

FIG. 1 is a schematic presentation of the female member of a basket for holding an ophthalmic lens according to a preferred embodiment of the invention.

FIG. 2 is a schematic presentation of the male member of a basket for holding an ophthalmic lens according to a preferred embodiment of the invention.

FIG. 3 is a section view of a basket according to a preferred embodiment of the invention.

DESCRIPTION OF THE PREFERRED EMBODIMENTS

Figure 1B:
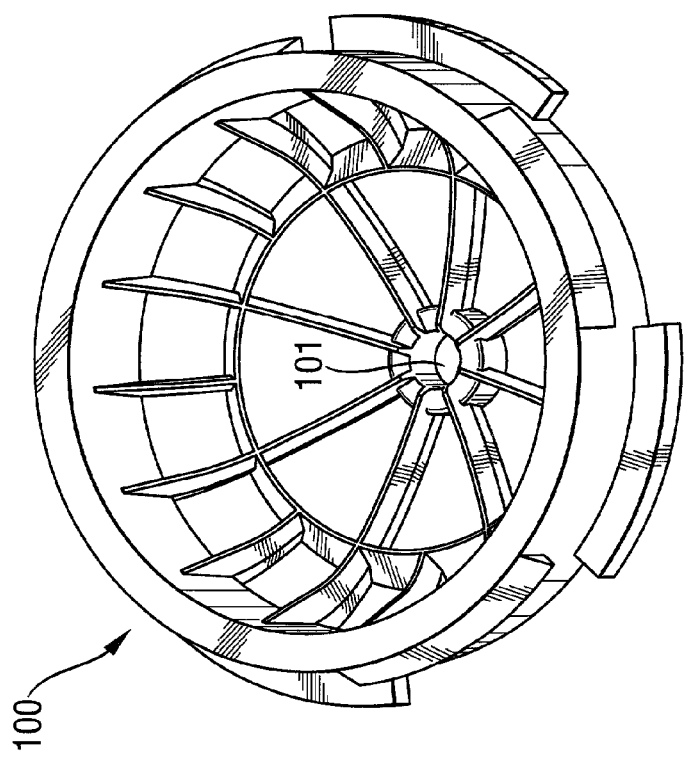
FIG. 1a is the bottom view (the lens-non-contacting side) of the female member and FIG. 1b is the top view (the lens-contacting side) of the female member.

The present invention, in one aspect, relates to baskets for holding medical devices. The basket of the present invention has a lattice structure, which has a medical device contacting side having sharp edges available for a medical device to contact and an opposite medical device non-contacting side. The baskets are useful in a manufacturing process such as washing, extracting, drying, plasma coating, LbL coating or the like, during the production of medical devices. The baskets have particular utility in the LbL coating of medical devices, especially ophthalmic lenses.

As used herein, "a medical device" refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic lenses. In a preferred embodiment, medical devices are ophthalmic lenses.

"An ophthalmic lens", as used herein, refers to a contact lens (hard or soft), an intraocular lens, or an aesthetic lens to change eye color. An ophthalmic lens generally has a first and a second optical surfaces.

As used herein, "a basket" refers to an assembly that comprises two or more members and a means for securing the members together to form a cavity for receiving a medical device, all members having openings for allowing fluid to pass through the basket while the medical device is in place. Preferably, a basket of the present invention comprises a first member and a second member and has a percentage of opening surface over total surface being at least 25%.

Baskets can be made from any easily fabricated material, including, without limitation, plastics, metal, ceramic, glass or similar materials. Preferably, the members of the baskets are made from a plastic material. Examples of suitable plastic materials include polystyrenes, polyolefines, acrylics, polycarbonates, polyacetal resins, polyacrylethers, polyacrylether sulfones, nelons, and the like. The most preferred material for the members of a basket is polycarbonate which can be machined or injection molded and can withstand the solvents and washing and coating solution within the temperature range utilized.

The shape of a basket is preferably designed to accommodate the shape of a medical device to be held.

In a more preferred embodiment of the present invention, the basket for holding an ophthalmic lens comprises a pair of mating members (i.e., a female member and a male member), and a means for securing the members together to form a cavity for receiving the ophthalmic lens. Such cavity inhibits inversion or rolling over of the ophthalmic lens when an ophthalmic lens is in placed. In an even more preferred embodiment of the invention, the male member can be inserted within the female member such that there is clearance for an ophthalmic lens between the two members, yet not enough so that the ophthalmic lens can invert or roll over. In a particularly preferred embodiment, there are throughholes in the centers of the female and male members, and the sharp edges available for an ophthalmic lens to contact are radial lines without nodes. Such radial lines without nodes can provide a minimal surface available for an ophthalmic lens to temporarily or permanently contact.

Figure 1A:
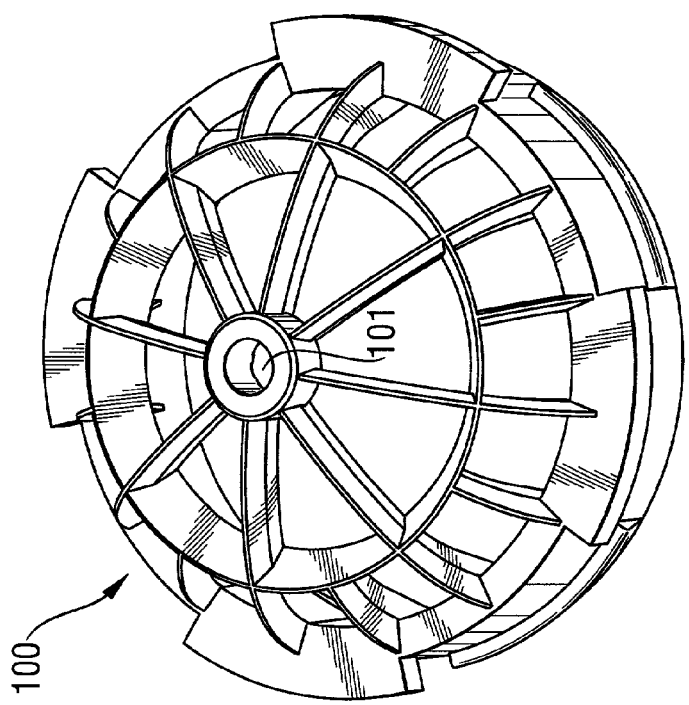
Figure 2B:
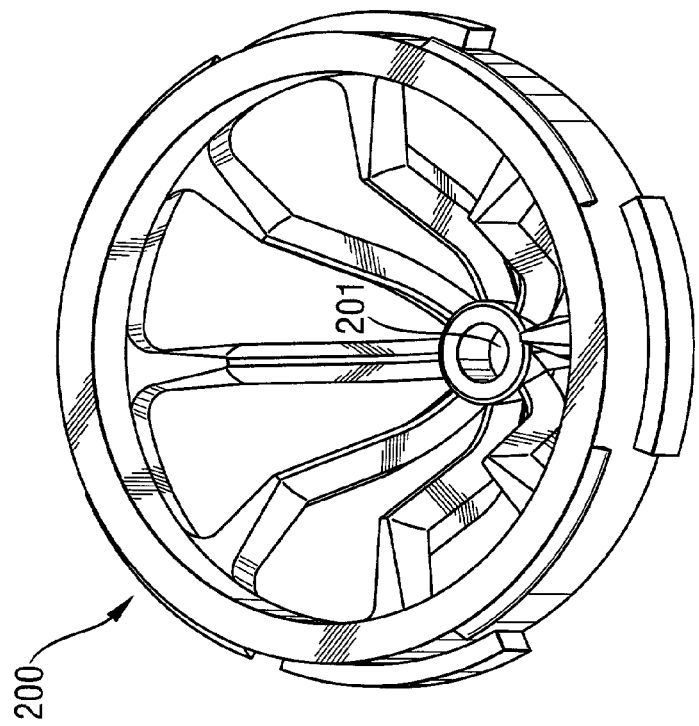
FIG. 2a is the bottom view (the lens-contacting side) of the male member and FIG. 2b is the top view (the lens-non-contacting side) of the male member.
Figure 2A:
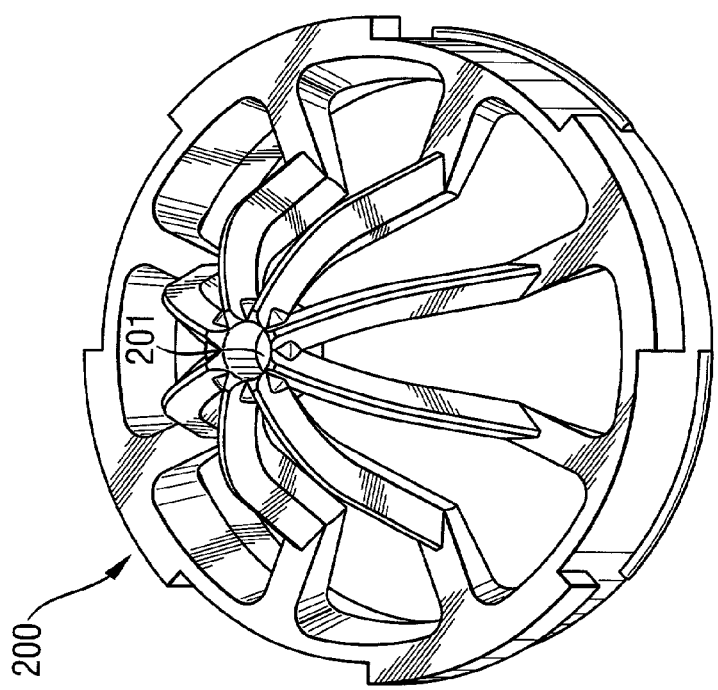
Figure 4:
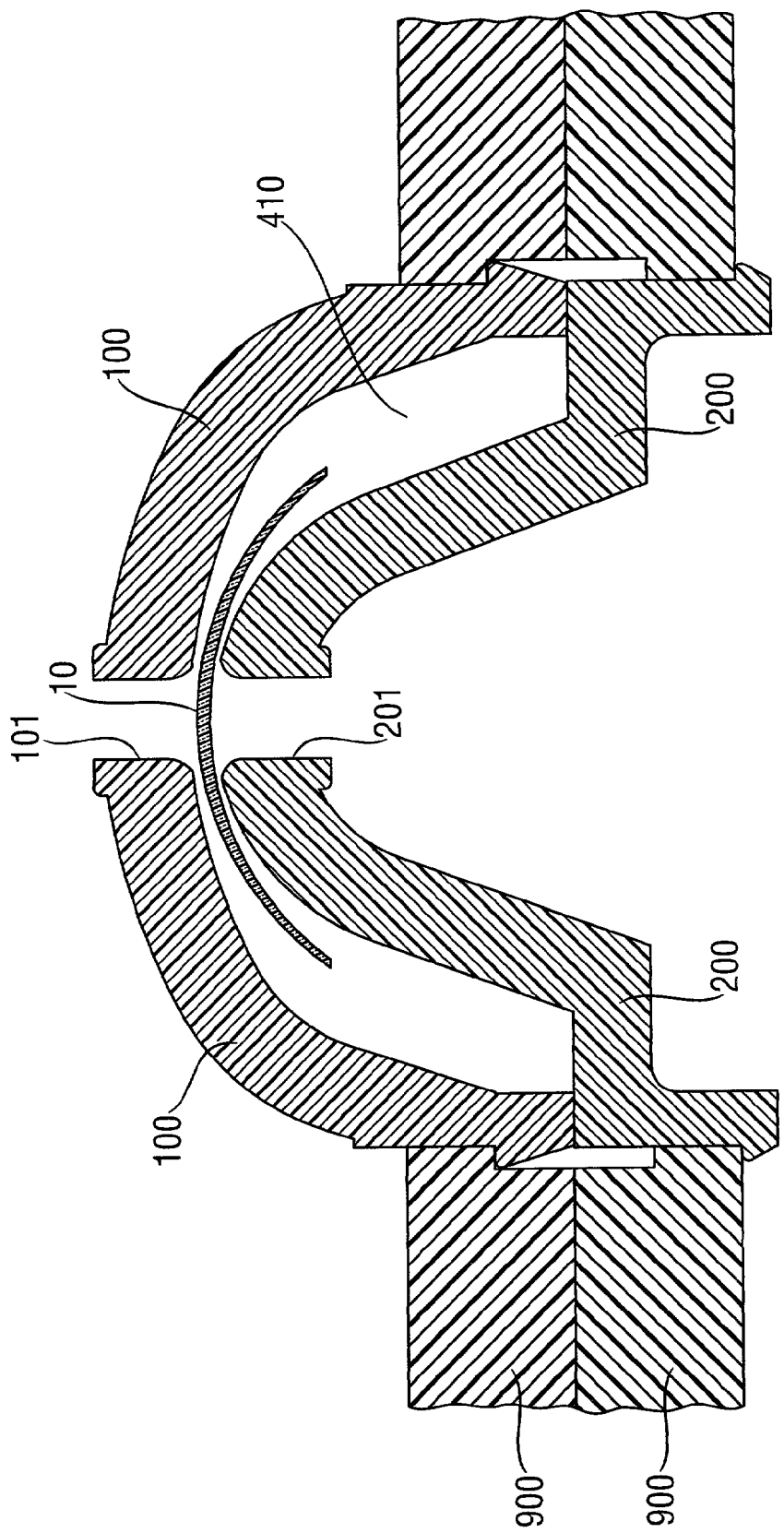
FIG. 4 is a cutaway view showing lens position between the male and female members and corresponding tolerance in a basket according to a preferred embodiment of the invention.
Figure 5:
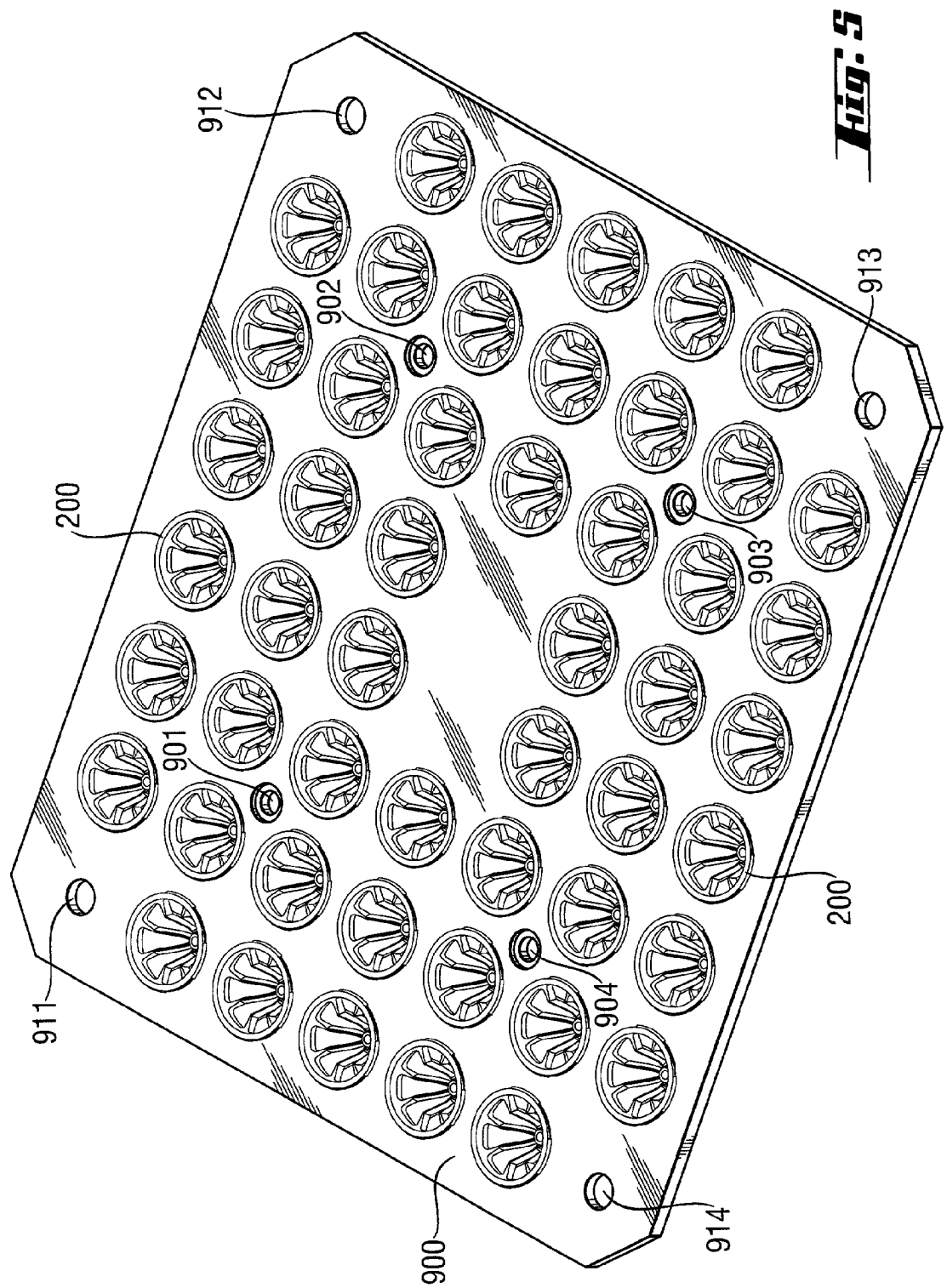
FIG. 5 is a schematic presentation of a portion of a tray containing male members of baskets (bottom view) according to a preferred embodiment of the invention.
Figure 6:
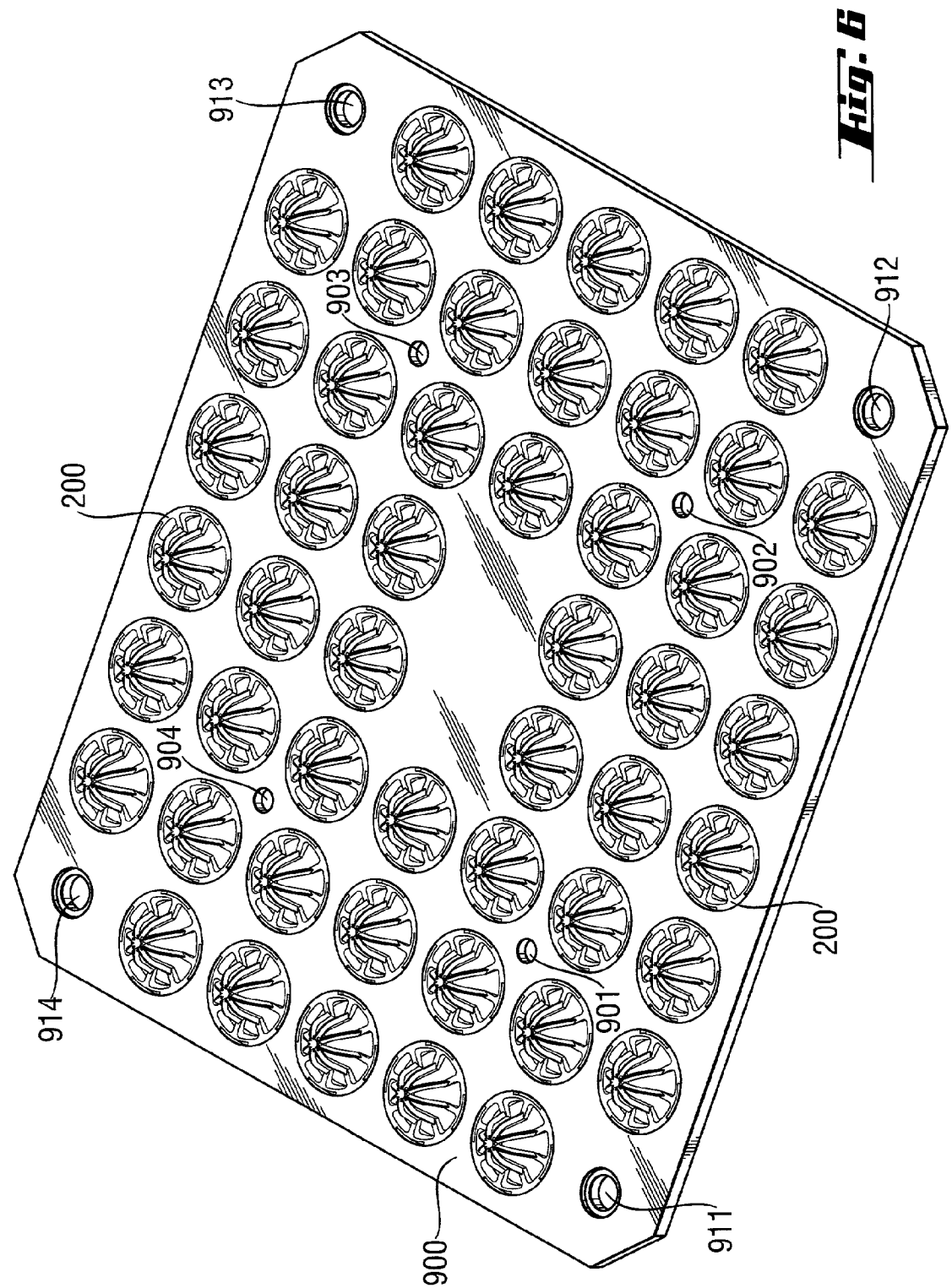
FIG. 6 is a schematic presentation of a portion of a tray containing male members of baskets (top view) according to a preferred embodiment of the invention.
Figure 7:
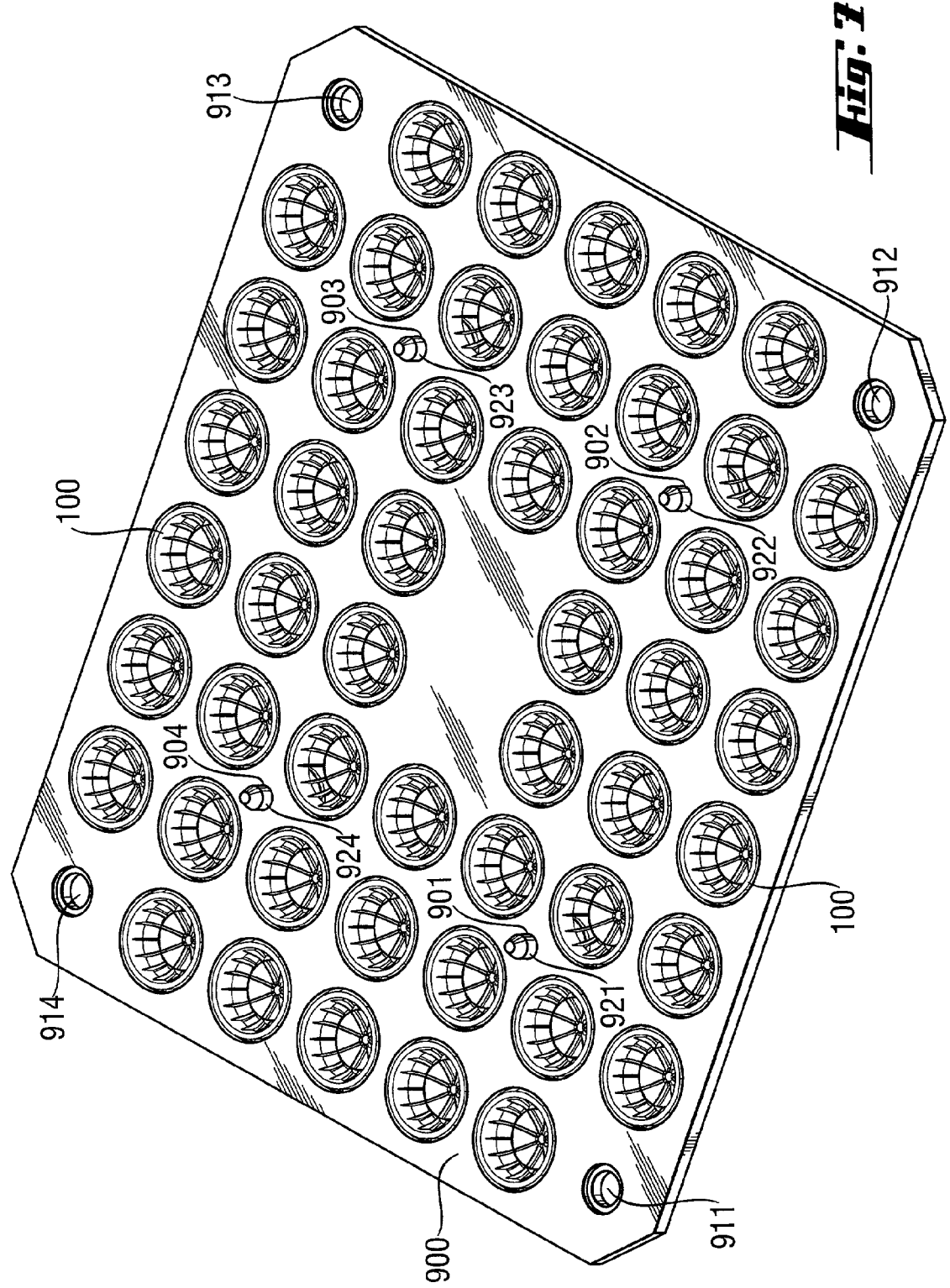
FIG. 7 is a schematic presentation of a portion of a tray containing female members of baskets (top view) according to a preferred embodiment of the invention.
Figure 8:
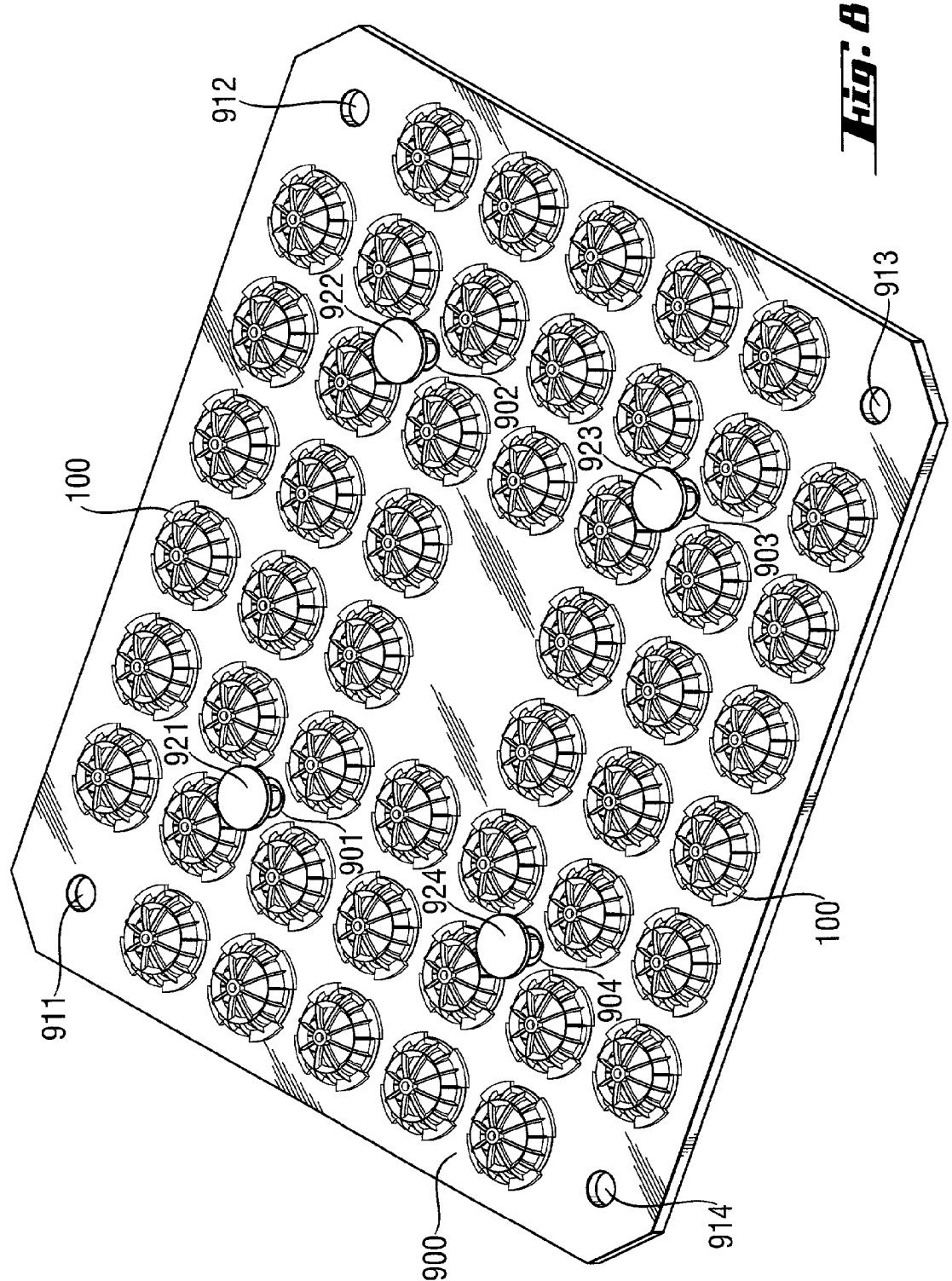
FIG. 8 is a schematic presentation of a portion of a tray containing female members of baskets (bottom view) according to a preferred embodiment of the invention.

FIGS. 1 and 2 schematically represent the female (100) and male (200) members of a basket for holding a contact lens according to a preferred embodiment of the invention. Through-holes (101, 201) are cut in the centers of the female and male members. The lens-contacting sides of both mating members are designed to have edges of radial lines without nodes. Such radial lines without nodes are only surface areas in a basket available for an ophthalmic lens to contact. FIGS. 3 and 4 schematically depict an assembly (basket) of the female member (100) and the male member (200). Ratio of open area to total surface area is calculated to be 80%, based on a projected flat surface pattern of the basket shown in FIGS. 1-4. A basket with such design can minimize the surface area onto which lens can stick and still maintain a sufficient mechanical strength.

Referring to FIG. 4, a lens (10) is located in a cavity (410) formed by mating the female member (100) and the male member (200). The cavity (410) has clearance for a lens (10) between the two members, but not enough for the lens (10) to invert or roll over when the lens is place therein.

Advantage of using a basket of the invention is that the adhesion of an ophthalmic lens to any part of the basket can be minimized and/or eliminated probably because there is not sufficient surface area with which a lens could maintain a permanent contact. By using baskets of the invention, ophthalmic lenses can be treated uniformly during a manufacturing process such as washing, extracting, coating, drying and the like, especially during a LbL coating process.

The present invention, in another aspect, relates to a tray for holding a plurality of medical devices, preferably ophthalmic lenses. A tray of the invention is useful for carrying out a process, such as washing, extracting, coating, drying and the like, particularly LbL coating, on batches containing a plurality of medical devices. Thus, the efficiency and productivity of the processing of medical devices, preferably ophthalmic lenses, can be substantially enhanced by using trays of the invention.

"A tray" as used herein refers to a assembly holding a plurality of baskets. A plurality of baskets can be intrinsic parts of a tray, or can be assembled together by one or more support members. "Support members" means any structural elements which together can hold a plurality of baskets. A plurality of baskets can be arranged in any way, for example, in rows or a matrix, in a tray.

Preferably, a tray of the invention comprises a first tray portion which holds the first members of a plurality of baskets, a second tray portion which holds the second members of the plurality of basket and a securing means for securing the first and second tray portions together to form the plurality of baskets for holding a plurality of medical devices.

More preferably, a tray of the invention comprises a first portion which holds the male members of a plurality of baskets, a second tray portion which holds the female members of the plurality of basket and a securing means for securing the first and second tray portions together to form the plurality of baskets. Each of the male members can be inserted within one female member such that there is clearance for an ophthalmic lens between the two members, yet not enough so that the ophthalmic lens can invert or roll over when emplaced therein.

Trays of invention can be made from any easily fabricated material, including, without limitation, plastics, metal, ceramic, glass or similar materials, preferably from a plastic material. Examples of suitable plastic materials include polystyrenes, polyolefines, acrylics, polycarbonates, polyacetal resins, polyacrylethers, polyacrylether sulfones, nelons, and the like. The most preferred material for making trays is polycarbonate which can be machined or injection molded and can withstand the solvents and washing and coating solution within the temperature range utilized.

Figure 9:
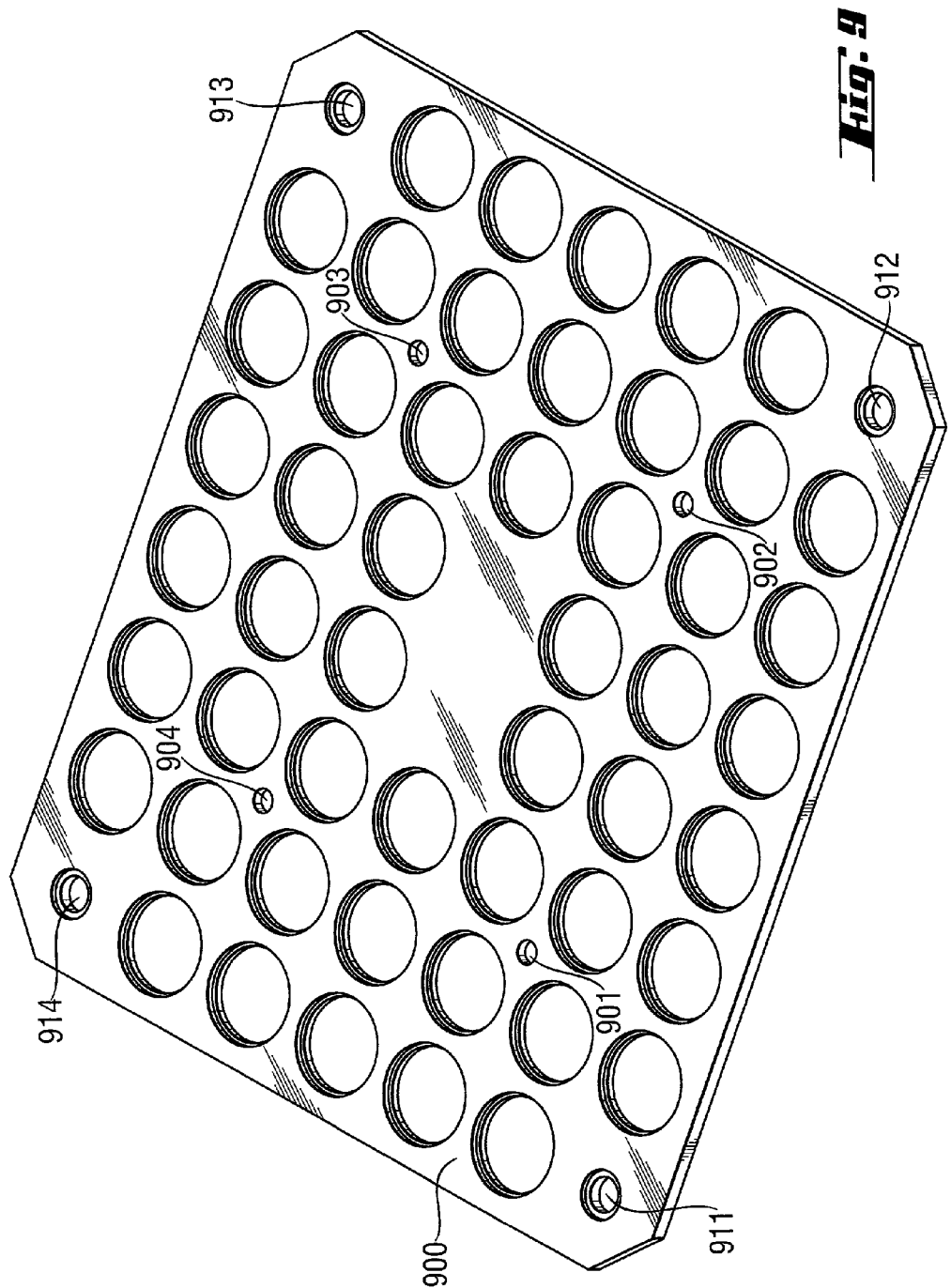
FIG. 9 is a schematic presentation of a support capable of holding female or male members of baskets for holding ophthalmic lenses.

FIGS. 5-8 schematically illustrate the two mating portions of a tray for holding ophthalmic lenses according to a preferred embodiment of the invention. A plurality of male basket members (200) are held by a first support 900 shown schematically in FIG. 9. A plurality of female basket members (100) are held by a second support 900. The two mating portions of a tray are secured together by securing means 921, 922, 923 and 924 through openings 901, 902, 903 and 904 in the supports. A matrix of through-holes in the support 900 shown in FIG. 9 are used to secure female or male basket members. Openings 911, 912, 913 and 914 in the supports 900 can be used in the securing of a plurality of trays to form a stack assembly.

The present invention, in still another aspect, relates to a stack assembly for holding medical devices, preferably ophthalmic lenses. The stack assembly of the invention comprises two or more trays of the invention and a stacking means for stacking together the trays. By using a stack assembly of the invention, large numbers of medical devices, preferably ophthalmic lenses can be processed simultaneously in a manufacturing process such as washing, extracting, coating, drying and the like, resulting high though-put efficiency of the manufacturing process.

The present invention, in a further aspect, relates to a method for cleaning baskets or trays or a stack assembly for holding medical devices, preferably ophthalmic lenses. The method of the invention comprises immersing the baskets or the trays or the stack assembly in an aqueous solution containing at least 1% weight/volume of KOH or $N_aOH$ for at least 5 minutes, removing the basket from the aqueous KOH or $N_aOH$ solution, and rising the basket with water to remove KOH or $N_aOH$ from the surface of the basket.

By using the cleaning method of the invention, even very dried, thick LbL coatings on baskets or trays can be removed without any scrubbing. This simple process allow to provide the baskets or trays with clean surfaces for every LbL coating runs.

In order to better enable the reader to understand specific embodiments and the advantages thereof, reference to the following non-limiting examples and drawings is suggested.

EXAMPLE 1

Synthesis of Macromers

Silicone-containing macromers, which are used in making contact lenses, are synthesized according to the procedures described in Example B-1 to B-4 of U.S. Pat. No. 5,849,811, herein incorporated by reference in its entirety.

Production of Contact Lenses

Contact lenses are prepared according to the procedures described in Example B-5 to B-14 of U.S. Pat. No. 5,849,811.

EXAMPLE 2

This example illustrates the comparison of the performance of a basket (Line contact) of the invention with two types of baskets (types I and II) in layer-by-layer (LBL) coating process. Types I and II baskets both are conventional designs. Type I baskets have holes to allow liquid pass through the baskets. In order to have a suitable mechanical strength, type I baskets have a small percentage of open area over total surface. Type II baskets have holes to allow liquid pass through the baskets and small bulges uniformly distributed on the lens contacting solid surface. Those small bulges provide direct lens support and can decrease lens-accessible surface area and may facilitate the movement of lens in the baskets.

LbL coatings on contact lenses are carried as follows. A contact lens held in one of three type of baskets is dipped first into a polyacrylic acid (PM) solution and then into a polyallylamine hydrochloride (PAH) solution. The time for coating the first layer of PM is about five minutes. The time for coating the second and subsequent layers of PAH and PM is also about five minutes. A rinsing step may be carried out between the dips in the first and second coating solutions. This procedure of dipping in an alternative fashion into the PM solution and PAH solution is repeated 4 times. A final layer of PM is coated on the lens. The coated lenses containing nine LbL layers (PAA/PAH/PAA/PAH/PAA/PAH/PAA/PAH/PM) are then released into a releasing and storage medium (e.g., pure water or a saline solution) where the coated lenses are stored.

After coating, dye stain tests are carried out to check if the lenses are uniformly and completely coated with LbL layers. A suitable amount of a dye, e.g., Sudan Black, is dissolved in vitamin E oil. Sudan Black is a hydrophobic dye and has a great affinity to silicone elastomers. Sudan Black can stain uncoated contact lenses to be tested. If contact lenses are coated uniformly and completely, the coated lenses have a hydrophilic coating that prevents Sudan Black from penetrating onto and into lenses and thereby from staining lenses. Any observed staining on a lens indicates failure in its LbL coating.

Table I shows the results obtained for three types of baskets. The basket with a line contact design has a lowest failing rate

TABLE I

Effects of basket designs on the efficiency of LBL coating of lenses

| Tray type | Type of basket | Percentage of openning[1] | Failing rates[2] | | | |
| --- | --- | --- | --- | --- | --- | --- |
| | | | Group 1 | Group 2 | Group 3 | Group 4 |
| 50 well tray | Line contact | 80% | 0/10* | 0/10 | 0/10 | 0/10* |
| 48 well tray | Type I | 24% | 2/10 | 4/10 | 2/14 | 6/14 |
| 52 well tray | Type II | 40% | 0/10* | 6/10 | 9/10 | 8/10 |

[1]This is a ratio of open area to total surface area, calculated based on a projected flat surface pattern of each basket.
[2]The failing rate is equal to the number of lenses failed divided by the number of total lenses tested in a group.
*No agitation during the LBL coating.

What is claimed is:

1. A basket for holding an ophthalmic lens, the basket having a lattice structure, wherein said basket comprises a first and a second mating members, said first and second mating members having an ophthalmic lens contacting side and an ophthalmic lens non-contacting side, said first and second mating members forming a cavity when mated for receiving said ophthalmic lens, said cavity inhibiting inversion or rolling over of said ophthalmic lens when emplaced therein, wherein said ophthalmic lens contacting side of said lattice has sharp edges available for said ophthalmic lens to contact, and further wherein said sharp edges are thin lines radiating from the centers of said first and second mating members, wherein each of the thin lines have a thickness of about 1/10 mm or less, and wherein there are through-holes in the centers of said first and second mating members.

2. A basket of claim 1, wherein the first mating member is capable of being inserted within the second mating member.

3. A basket of claim 2, wherein the lens-contacting side of the second mating member has a concave curvature.

4. A basket of claim 3, wherein the lens-contacting side of the first mating member has a convex curvature.

5. A tray, for holding a plurality of ophthalmic lenses, comprising a plurality of baskets each capable of holding one of said ophthalmic lenses, wherein each of said baskets has a lattice structure, wherein said lattice has an ophthalmic lens-contacting side and an opposite ophthalmic lens non-contacting side, and wherein said ophthalmic lens-contactinq side of said lattice has very sharp edges available for one of said ophthalmic lenses to contact, and wherein said tray comprises a first mating portion and a second mating portion, said first mating portion comprising male basket members and said second mating portion comprising female basket members, the numbers of said male basket members and said female basket members being equal, and wherein when mated said first and second mating portions forms said plurality of baskets each having a cavity for receiving one of said ophthalmic lenses, said cavity inhibiting inversion and rolling over of one of said ophthalmic lenses when emplaced therein, and further wherein said sharp edges are thin lines radiating from the centers of said male and female basket members, wherein each of the thin lines have a thickness of about 1/10 mm or less, and wherein there are through-holes in the centers of said male and female basket members.

6. A tray of claim 5, wherein each of the male basket members is capable of being inserted within one of the female basket members.

7. A tray of claim 6, wherein the lens-contacting side of each of the female basket members has a concave curvature.

8. A tray of claim 7, wherein the lens-contacting side of each of the male basket members has a convex curvature.

\* \* \* \* \*